US006930199B2

(12) United States Patent
Meyn et al.

(10) Patent No.: US 6,930,199 B2
(45) Date of Patent: Aug. 16, 2005

(54) PROCESS FOR THE PREPARATION OF DIISOCYANATES

(75) Inventors: Jürgen Meyn, Dormagen (DE); Herbert Stutz, Dormagen (DE)

(73) Assignee: Bayer MaterialSceince AG, Leverkusen (DE)

( * ) Notice: Subject to any disclaimer, the term of this patent is extended or adjusted under 35 U.S.C. 154(b) by 0 days.

(21) Appl. No.: 11/010,937

(22) Filed: Dec. 13, 2004

(65) Prior Publication Data

US 2005/0137417 A1   Jun. 23, 2005

(30) Foreign Application Priority Data

Dec. 18, 2003 (DE) ................ 103 59 627

(51) Int. Cl.[7] .......................................... C07C 263/00
(52) U.S. Cl. ...................................................... 560/347
(58) Field of Search ........................................ 560/347

(56) References Cited

U.S. PATENT DOCUMENTS

| 4,847,408 A | 7/1989 | Frosch et al. ............... 560/347 |
| 5,391,683 A | 2/1995 | Joulak et al. ................. 528/67 |
| 5,633,396 A | 5/1997 | Bischof et al. ............. 560/347 |

OTHER PUBLICATIONS

Justus Liebigs Annalen der Chemie, 562, (month unavailable) 1949, p. 108, Werner Siefken, Mono- und Polyisocyanate.

Primary Examiner—Paul A. Zucker
(74) Attorney, Agent, or Firm—Joseph C. Gil; Thomas W. Roy

(57) ABSTRACT

The invention relates to a process for the preparation of isocyanates in the gas phase, in which the possibilities for back-mixing and byproduct formation are reduced by improving the mixing of the starting materials in a tubular reactor.

15 Claims, 1 Drawing Sheet

PROCESS FOR THE PREPARATION OF DIISOCYANATES

CROSS REFERENCE TO RELATED PATENT APPLICATION

The present patent application claims the right of priority under 35 U.S.C. § 119 (a)–(d) of German Patent Application No.103 59 627.5, filed Dec. 18, 2003.

BACKGROUND OF THE INVENTION

1. Field of the Invention

The present invention relates to a process for the preparation of diisocyanates and/or triisocyanates by phosgenation of the corresponding diamines and/or triamines in the gas phase.

2. Description of the Prior Art

The preparation of isocyanates by reaction of amines with phosgene in the gas phase has long been known (cf. Siefken, Annalen 562, 108 (1949). Gas-phase reactions can be carried out in various ways. Nozzles, burners or mixing tubes are used for mixing the starting materials. For the gas-phase phosgenation of diisocyanates, the use of nozzles has been very generally described. These are, as described, for example, in EP-A1-0593334, smooth jet nozzles or concentric feed tubes. Usually, one of the starting materials is sprayed through a centrally arranged nozzle into the stream of the second starting material which flows through the annular space around the nozzle tube at low velocity. The faster-flowing starting material aspirates the slow-flowing starting material, and mixing occurs. After a time or distance dependent on the nozzle diameter and on the difference between the flow velocities of the starting materials, complete mixing of the starting materials is then achieved. The chemical reaction is superposed on the mixing. The gas-phase phosgenation of amines is a reaction whose rate is determined by the mixing of the starting materials. Since the isocyanates formed can undergo secondary reactions with the amines, rapid mixing and an excess of phosgene are necessary for achieving a high selectivity with respect to the desired diisocyanate. Owing to back-mixing processes, the diisocyanate reacts with unreacted diamine from the starting material stream with formation of solid deposits. This results in soiling of the reactor below the mixing zone and in blockages of the reactor.

On an increase of the size of the reactor, which is frequently in the form of a tubular reactor, an increase in the size of the mixing nozzle, which is frequently in the form of a smooth jet nozzle, is also necessary. With the increase in the diameter of the smooth jet nozzle, however, the rate of mixing of the central jet is reduced by the greater diffusion distance required and the danger of back-mixing is increased, which in turn leads to the formation of polymeric impurities and hence caking of solid materials in the reactor.

In British Patent Specification 1165831, the reaction is carried out in a tubular reactor equipped with a mechanical stirrer. The reactor resembles a thin-film evaporator in which the stirrer mixes the gases and at the same time scrapes against the heated walls of the tubular reactor in order thus to prevent a build-up of polymeric material on the tube wall. However, the use of a high-speed stirrer when handling phosgene at about 300° C. requires a high level of safety measures in order to seal the reactor and to mount the stirrer in the highly corrosive medium.

It is therefore an object of the present invention to provide a process for the preparation of diisocyanates and/or triisocyanates in the gas phase, in which the starting materials diamine and phosgene can be mixed more rapidly and better in a reactor without moving internals and in which the formation of polymeric impurities and of caking of the reactor can be avoided.

SUMMARY OF THE INVENTION

The present invention is directed to a process for the preparation of diisocyanates and triisocyanates of the general formula (I)

$$R(NCO)_n \quad (I),$$

where R represents a (cyclo)aliphatic or aromatic hydrocarbon radical having up to 15 carbon atoms with the proviso that at least 2 carbon atoms are arranged between two NCO groups, and n represents the number 2 or 3.

The process is carried out in a a tubular reactor which has a double-walled guide tube extending centrally in the direction of the axis of rotation of the tubular reactor, a concentric annular gap being formed between the inner and the outer wall of the double-walled guide tube, and the ratio of the cross-sectional area of the tubular reactor, which area is bounded by the inner wall of the double-walled guide tube, to the cross-sectional area of the tubular reactor, which area is bounded by the wall of the tubular reactor and the outer wall of the double-walled guide tube, being 1:0.5 to 1:4, The process steps include gas phase phosgenating the corresponding diamines and/or triamines of the general formula (II)

$$R(NH_2)_n \quad (II),$$

where R represents a (cyclo)aliphatic or aromatic hydrocarbon radical having up to 15 with the proviso that at least two carbon atoms are arranged between two amino groups, and n represents the number 2 or 3, by heating the diamines and/or triamines in vapour form and phosgene separately from one another to temperatures of 200° C. to 600° C., feeding the diamines and/or triamines in vapour form are to the tubular reactor via the concentric annular gap at a mean flow velocity of 20–150 m/s, and feeding the phosgene is to the tubular reactor over the remaining cross-sectional areas of the tubular reactor at a mean flow velocity of at least 1 m/s.

DETAILED DESCRIPTION OF THE INVENTION

Figure 1:
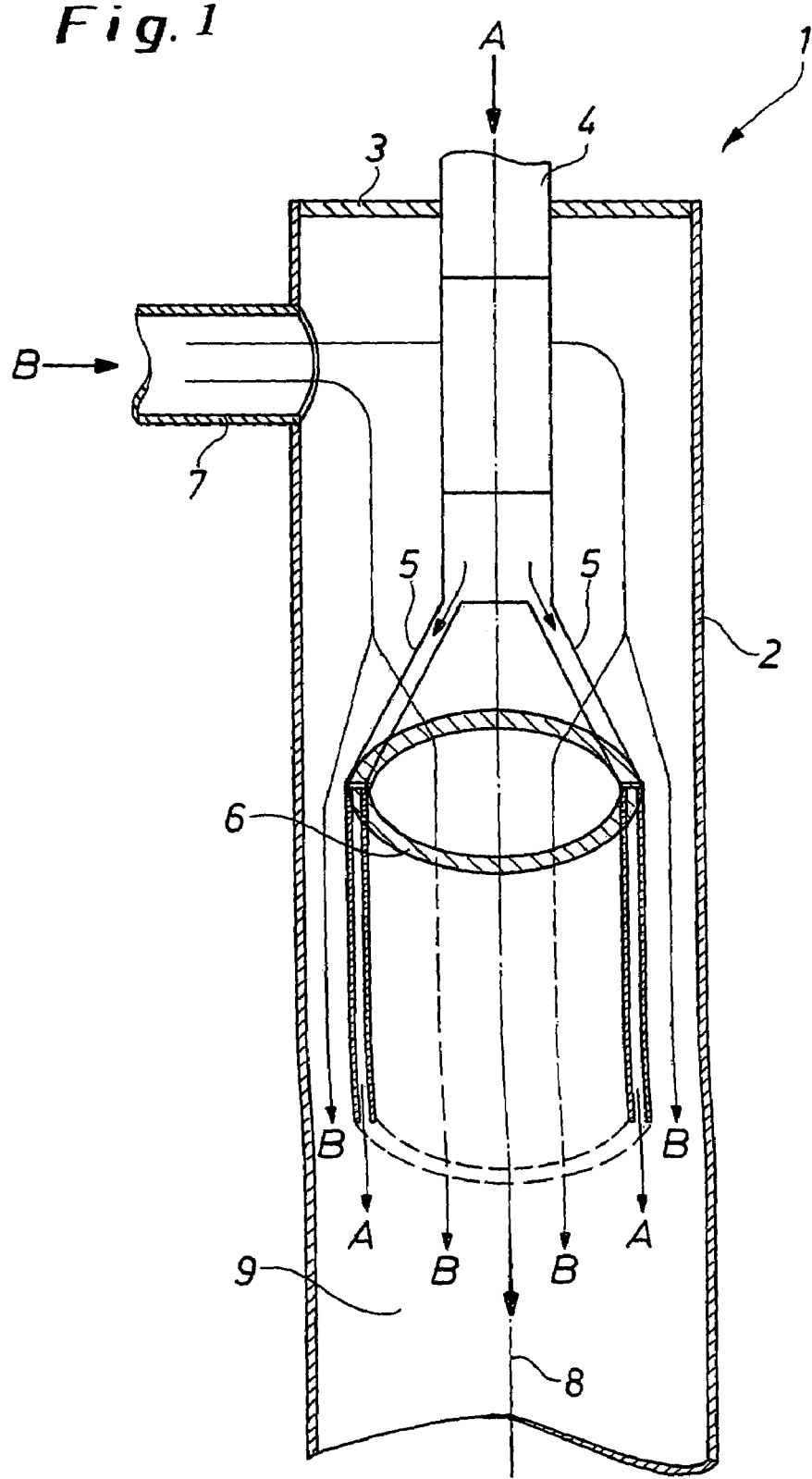
FIG. 1 is a schematic showing a tubular reactor which is suitable for use in the process according to the invention.

Other than in the operating examples, or where otherwise indicated, all numbers or expressions referring to quantities of ingredients, reaction conditions, etc. used in the specification and claims are to be understood as modified in all instances by the term "about."

It has now been found that it is possible to prepare (cyclo)aliphatic or aromatic diisocyanates and/or triisocyanates by gas-phase phosgenation of the corresponding diamines and/or triamines with elimination of said disadvantages of the prior art if one starting material stream is mixed in at high velocity by an annular gap which is positioned concentrically in the stream of the other starting material. Consequently, the diffusion distance for the mixing is small and the mixing times are very short. The reaction can then take place with high selectivity to give the desired diisocyanate. The formation of polymeric impurities and caking are thus reduced.

The invention relates to a process for the preparation of diisocyanates and triisocyanates of the general formula (I)

$$R(NCO)_n \qquad (I),$$

in which
R represents a (cyclo)aliphatic or aromatic hydrocarbon radical having up to 15 carbon atoms, preferably 4 to 13 carbon atoms, with the proviso that at least 2 carbon atoms are arranged between two NCO groups, and
n represents the number 2 or 3,
by phosgenation of the corresponding diamines and/or triamines of the general formula (II)

$$R(NH_2)_n \qquad (II),$$

in which
R represents a (cyclo)aliphatic or aromatic hydrocarbon radical having up to 15, preferably 4 to 13, carbon atoms, with the proviso that at least two carbon atoms are arranged between two amino groups, and
n represents the number 2 or 3,
in the gas phase in a tubular reactor which has a double-walled guide tube extending centrally in the direction of the axis of rotation of the tubular reactor, a concentric annular gap being formed between the inner and the outer wall of the double-walled guide tube, and the ratio of the cross-sectional area of the tubular reactor, which area is bounded by the inner wall of the double-walled guide tube, to the cross-sectional area of the tubular reactor, which area is bounded by the wall of the tubular reactor and the outer wall of the double-walled guide tube, being 1:0.5 to 1:4, preferably 1:1 to 1:3,
in which the diamines and/or triamines in vapour form and phosgene are heated separately from one another to temperatures of 200° C. to 600° C.,
and the diamines and/or triamines in vapour form are fed to the tubular reactor via the concentric annular gap at a mean flow velocity of 20–150 m/s, preferably 40–100 m/s, and phosgene is fed to the tubular reactor over the remaining cross-sectional areas of the tubular reactor at a mean flow velocity of at least 1 m/s, preferably 5–15 m/s.

The diamines in vapour form may also optionally be diluted with an inert gas or with the vapours of an inert solvent before being fed to the tubular reactor. Suitable inert gases are, for example, nitrogen or noble gases, such as helium or argon. Nitrogen is preferably used. Suitable solvents are, for example, chlorobenzene, o-dichlorobenzene, toluene, xylene, chlorotoluene, chloronaphthalene and decahydronaphthalene. Chlorobenzene is preferably used.

In the process according to the invention, the mixing of the two gaseous starting materials takes place at the annular separation surfaces of the diamine and phosgene starting material jets.

Starting materials for the process according to the invention are diamines and/or triamines of the general formula (II)

$$R(NH_2)_n \qquad (II)$$

in which
R represents a (cyclo)aliphatic or aromatic hydrocarbon radical having up to 15, preferably 4 to 13, carbon atoms, with the proviso that at least two carbon atoms are arranged between two amino groups, and
n represents the number 2 or 3.

Typical examples of suitable aliphatic diamines are mentioned in EP-A1-0289840, in column 3, lines 19 to 26. Examples of suitable aliphatic triamines are mentioned, for example, in EP-A-749 958, in column 3, lines 18 to 22 and lines 28 to 31. 1,4-Diaminobutane, 1,3-diaminopentane, 1,6-diaminohexane (HDA), 1,11-diaminoundecane, 1,4-diaminocyclohexane, 1-amino-3,3,5-trimethyl-5-aminomethylcyclohexane (isophoronediamine, IPDA), 2,3-, 2,4- and 2,6-diamino-1-methylcyclohexane and mixtures thereof, 1,3,5-triisopropyl-2,4-diaminocyclohexane, 2,4- and 2,6-diamino-1-isopropylcyclo-hexane or mixtures thereof and bis(p-aminocyclohexyl)methane are particularly suitable.

Isophoronediamine (IPDA), hexamethylenediamine (HDA) and bis(p-aminocyclohexyl)methane are preferred.

Typical examples of suitable aromatic diamines are the pure isomers or isomer mixtures of diaminobenzene, of diaminotoluene, of diaminodimethylbenzene, of diaminonaphthalene and of diaminodiphenylmethane; 2,4/2,6-toluenediamine mixtures having the isomer ratios 80/20 and 65/35 or the pure 2,4-toluenediamine isomers are preferred.

The triamine used is preferably 1,8-diamino-4-(aminomethyl)octane or triaminononane.

The starting amines are vaporized before carrying out the process according to the invention and are heated to 200° C. to 600° C., preferably 300° C. to 500° C., and optionally diluted with an inert gas or with the vapours of an inert solvent before being fed to the reactor.

The phosgene used in the phosgenation is likewise heated to a temperature within the range from 200° C. to 600° C., preferably 300° C. to 500° C., before carrying out the process according to the invention.

For carrying out the reaction according to the invention, the preheated stream containing di- and/or triamines or mixtures of di- and/or triamines and the preheated stream containing phosgene are passed continuously into the tubular reactor.

The tubular reactors generally consist of steel, glass, alloyed or enamelled steel and have a length which is sufficient for permitting complete reaction of the diamine with the phosgene under the process conditions. The phosgene stream is generally fed in at one end of the tubular reactor. The amine is mixed in at high velocity into this phosgene stream via a concentric annular gap positioned radially symmetrically. The phosgene is fed to the tubular reactor both over the cross-sectional area which is bounded by the inner wall of the double-walled guide tube and over the cross-sectional area which is bounded by the wall of the tubular reactor and the outer wall of the double-walled guide tube.

The mixing zone is preferably kept at a temperature within the range from 200° C. to 600° C., preferably 300° C. to 500° C., it being possible, if required, for this temperature to be maintained by heating the tubular reactor.

When the process according to the invention is carried out, the pressure in the feed lines to the tubular reactor is preferably 200 mbar to 4000 mbar and that at the exit from the tubular reactor is 150 mbar to 2000 mbar. By maintaining a suitable pressure difference, a flow velocity of the phosgene stream at the entrance into the tubular reactor of at least 1 m/s, preferably 2 m/s to 60 m/s, particularly preferably 3 to 20 m/s, very particularly preferably 5 to 15 m/s, is established.

The amine is mixed in via a concentric annular gap at a velocity of 20–150 m/s, preferably 40–100 m/s. The mixing of the two gaseous starting materials diamine and phosgene takes place at the annular separation surfaces of the starting material jets.

Under these reaction conditions, turbulent flow conditions generally prevail within the reaction space.

The invention is explained below with reference to FIG. 1.

FIG. 1 shows a tubular reactor 1 which is suitable for use in the process according to the invention. The tubular reactor 1 contains a cylindrical wall 2 which surrounds the reaction space 9 and a cover 3 which seals the cylindrical reaction space at one end of the cylindrical wall 2 from the outside. The tubular reactor 1 is open on the side opposite to the cover 3. An orifice which is filled by a cylindrical tube section 4 projecting on both sides of the cover 3 is arranged centrally in the cover 3, i.e. rotationally symmetrically relative to the axis 8 of rotation of the cylindrical wall 2. On the side projecting into the reaction space 9, the tube section 4 opens via connecting pipes 5 into a double-walled guide tube 6 which is arranged centrally in the reaction space 9, i.e. rotationally symmetrically relative to the axis 8 of rotation of the cylindrical wall 2. The tubular reactor 1 furthermore has, at the height of the tube section 4, an inlet nozzle 7 arranged on the cylindrical wall 2.

The stream A containing diamines and/or triamines flows through the tube section 4, the connecting pipes 5 and the double-walled guide tube 6 and finally emerges from the double-walled guide tube in the form of an annular jet. The phosgene-containing stream B flows in approximately at the height of the tube section 4 through the inlet nozzle 7 directly into the space between the cylindrical wall 2 and the tube section 4 and flows around the tube section 4, the connecting pipes 5 and the double-walled guide tube 6. The flow around the double-walled guide tube 6 is both through the free cross-sectional area which is bounded by the inner wall of the double-walled guide tube, and through the free cross-sectional area which is bounded by the cylindrical wall 2 of the tubular reactor and the outer wall of the double-walled guide tube. The flow paths of the starting materials A and B are indicated by the arrows in the form of flow lines in the figure. The stream A containing the di- and/or triamines emerges from the double-walled guide tube 6 in the form of a free annular jet and then mixes, with generally turbulent flow, with the phosgene-containing stream B, the corresponding di- and/or triisocyanates forming.

EXAMPLES

Example 1

Example According to the Invention

An isophoronediamine/inert gas mixture, as starting material stream A, and phosgene as starting material stream B are passed continuously into a tubular reactor according to FIG. 1, comprising a downstream isocyanate condensation stage and isocyanate working-up downstream thereof. The temperatures of the two starting material streams are 300° C. The pressure in the tubular reactor is slightly above atmospheric pressure at 1400 mbar.

The velocity of the component A in the double-walled guide tube 6 is about 60 m/s and that of component B prior to mixing is about 7 m/s. The ratio of the cross-sectional area of the tubular reactor 1, which area is bounded by the inner wall of the double-walled guide tube 6, to the cross-sectional area of the tubular reactor, which area is bounded by the cylindrical wall 2 of the tubular reactor and the outer wall of the double-walled guide tube, is 1:1.

The velocity of the reaction mixture at the reactor exit is about 17 m/s.

After leaving the reactor, the reaction product isophorone diisocyanate (IPDI) is condensed, separated from excess phosgene and the byproduct hydrogen chloride and then fed to a purification stage. The temperature on the cylindrical outer wall 2 of the tubular reactor 1 is measured with the aid of thermocouples at four temperature measuring points located downstream of the double-walled guide tube 6. The maximum temperature is reached at the second temperature measuring point, which is located about two diameters of the cylindrical wall 2 away from the mixing point in the downstream direction. The yield of IPDI, based on the IPDA used, is 98.8% of theory.

Example 2

Comparative Example

Example 1 is repeated under the same conditions, a smooth jet nozzle being used instead of the double-walled guide tube. The cross-sectional flow areas for the isophoronediamine/inert gas mixture and phosgene at the exit from the nozzle are equal to the cross-sectional flow areas in the tubular reactor according to example 1.

It is found that, with the use of the conventional smooth jet nozzle at comparable velocities of the components at the mixing point, the maximum temperature in the tubular reactor is reached only substantially later, namely only about five diameters of the cylindrical wall 2 away from the mixing point in the downstream direction. The yield of IPDI, based on the IPDA used, is 98.5% of theory.

In addition, it is found that the formation of polymeric byproducts which are deposited on the wall of the tubular reactor is reduced by the better and faster mixing with the use, according to the invention, of the tubular reactor having a double-walled guide tube. This results in a longer operating life of the reactor.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of diisocyanates and triisocyanates of the general formula (I)

$$R(NCO)_n \qquad (I),$$

in which

R represents a (cyclo)aliphatic or aromatic hydrocarbon radical having up to 15 carbon atoms with the proviso that at least 2 carbon atoms are arranged between two NCO groups, and n represents the number 2 or 3, the process comprising gas phase phosgenating the corresponding diamines and/or triamines of the general formula (II)

$$R(NH_2)_n \qquad (II),$$

in which

R represents a (cyclo)aliphatic or aromatic hydrocarbon radical having up to 15 with the proviso that at least two carbon atoms are arranged between two amino groups, and n represents the number 2 or 3, by providing a tubular reactor which has a double-walled guide tube extending centrally in the direction of the axis of rotation of the tubular reactor, a concentric annular gap being formed between the inner and the outer wall of the double walled guide tube, and the ratio of the cross-sectional area of the tubular reactor, which area is bounded by the inner wall of the double-walled guide tube, to the cross-sectional area of the tubular reactor, which area is bounded by the wall of the tubular reactor and the outer wall of the double-walled guide tube, being 1:0.5 to 1:4, heating the diamines and/or triamines in vapour form and phosgene separately from one another to temperatures of 200° C. to 600° C., feeding the diamines and/or triamines in vapour form to the tubular reactor via the concentric annular gap at a mean flow velocity of 20–150 m/s, and feeding the phosgene to the tubular reactor over the remaining cross-sectional areas of the tubular reactor at a mean flow velocity of at least 1 m/s.

2. The process according to claim 1, in which the mean flow velocity of the diamines and/or triamines in vapour form is 40 to 100 m/s.

3. The process according to claim 1, in which the mean flow velocity of the phosgene is 5 to 15 m/s.

4. The process according claim 1, in which isophoronediamine, hexamethylenediamine or bis(p-aminocyclohexyl) methane are used as diamines.

5. The process according to claim 1, in which 1,8-diamino-4-(aminomethyl)octane or triaminononane are used as triamines.

6. The process according to claim 1, wherein the phosgenating is carried out in a tubular reactor in which the ratio of the cross-sectional area of the tubular reactor, which area is bounded by the inner wall of the double-walled guide tube, to the cross-sectional area of the tubular reactor, which area is bounded by the wall of the tubular reactor and the outer wall of the double-walled guide tube, is 1:1 to 1:3.

7. The process according to claim 2, in which the mean flow velocity of the phosgene is 5 to 15 m/s.

8. The process according claim 2, in which isophoronediamine, hexamethylenediamine or bis(p-aminocyclohexyl) methane are used as diamines.

9. The process according claim 3, in which isophoronediamine, hexamethylenediamine or bis(p-aminocyclohexyl) methane are used as diamines.

10. The process according to claim 2, in which 1,8-diamino-4-(aminomethyl)octane or triaminononane are used as triamines.

11. The process according to claim 3, in which 1,8-diamino-4-(aminomethyl)octane or triaminononane are used as triamines.

12. The process according to claim 2, wherein the phosgenating is carried out in a tubular reactor in which the ratio of the cross-sectional area of the tubular reactor, which area is bounded by the inner wall of the double-walled guide tube, to the cross-sectional area of the tubular reactor, which area is bounded by the wall of the tubular reactor and the outer wall of the double-walled guide tube, is 1:1 to 1:3.

13. The process according to claim 3, wherein the phosgenating is carried out in a tubular reactor in which the ratio of the cross-sectional area of the tubular reactor, which area is bounded by the inner wall of the double-walled guide tube, to the cross-sectional area of the tubular reactor, which area is bounded by the wall of the tubular reactor and the outer wall of the double-walled guide tube, is 1:1 to 1:3.

14. The process according to claim 1, wherein the phosgenating is carried out in a tubular reactor in which the ratio of the cross-sectional area of the tubular reactor, which area is bounded by the inner wall of the double-walled guide tube, to the cross-sectional area of the tubular reactor, which area is bounded by the wall of the tubular reactor and the outer wall of the double-walled guide tube, is 1:1 to 1:3.

15. The process according to claim 1, wherein R is from 4 to 13 carbon atoms.

* * * * *